United States Patent
O'Neil et al.

(10) Patent No.: US 12,114,928 B2
(45) Date of Patent: Oct. 15, 2024

(54) OCULAR FOCUS ASSESSMENT AND MONITORING FOR MYOPIA AND OTHER VISION DISORDERS

(71) Applicants: James W. O'Neil, Phoenix, AZ (US); Richard S. Tirendi, Paradise Valley, AZ (US)

(72) Inventors: James W. O'Neil, Phoenix, AZ (US); Richard S. Tirendi, Paradise Valley, AZ (US)

(*) Notice: Subject to any disclaimer, the term of this patent is extended or adjusted under 35 U.S.C. 154(b) by 218 days.

(21) Appl. No.: 17/694,591

(22) Filed: Mar. 14, 2022

(65) Prior Publication Data

US 2022/0287558 A1 Sep. 15, 2022

Related U.S. Application Data

(60) Provisional application No. 63/164,413, filed on Mar. 22, 2021, provisional application No. 63/160,804, filed on Mar. 13, 2021.

(51) Int. Cl.
*A61B 3/032* (2006.01)

(52) U.S. Cl.
CPC .................... *A61B 3/0325* (2013.01)

(58) Field of Classification Search
CPC .................................... A61B 3/0325
USPC ......................................... 351/242
See application file for complete search history.

(56) References Cited

U.S. PATENT DOCUMENTS

| | | | |
|---|---|---|---|
| 9,517,008 B1* | 12/2016 | Berme | A61B 8/10 |
| 10,631,723 B1 | 4/2020 | Tirendi et al. | |
| 2008/0002153 A1* | 1/2008 | Kanazawa | H04N 13/327 |
| | | | 351/239 |
| 2008/0259277 A1* | 10/2008 | Inagaki | A61B 3/032 |
| | | | 351/232 |
| 2012/0075586 A1* | 3/2012 | Kirschen | A61B 3/028 |
| | | | 351/239 |
| 2016/0120402 A1* | 5/2016 | Limon | A61B 3/0033 |
| | | | 351/239 |
| 2018/0101721 A1 | 4/2018 | Nienhouse | |
| 2019/0175011 A1* | 6/2019 | Jensen | G10L 15/22 |

(Continued)

OTHER PUBLICATIONS

Vinas, Maria, et al., "Longitudinal chromatic aberration of the human eye in the visible and near infrared from wavefront sensing, double-pass and psychophysics", Optics Express, published Feb. 24, 2015, vol. 23, No. 4, pp. 948-962.

(Continued)

*Primary Examiner* — William R Alexander
*Assistant Examiner* — Sharrief I Broome
(74) *Attorney, Agent, or Firm* — Bycer & Marion, PLC; Matthew L. Bycer (57) ABSTRACT

A system and method for home testing of patient focal length, and detecting for the presence or changes in myopic conditions utilizing a multi-colored testing screen. Utilizing the varied refractive properties of each wavelength of light (colors), changes in myopia and focal length can be monitored in each of the separate colors. Baseline visual acuity is determined, and the testing occurs with relevant-sized optotypes. Optotypes are displayed in red, white, and green, simultaneously on a display screen set at four meters distance. Games and acuity tests are conducted to determine the focal acuity at each of the wavelengths. Results are recorded and used for future diagnosis and treatment.

23 Claims, 8 Drawing Sheets

(56) References Cited

U.S. PATENT DOCUMENTS

2019/0216381 A1 7/2019 Benford
2020/0029802 A1* 1/2020 Lane ..................... A61B 3/02

OTHER PUBLICATIONS

Holladay, Jack, "Proper Method for Calculating Average Visual Acuity", Journal of Refractive Surgery, published Jul./Aug. 1997, vol. 13, pp. 388-391.

Shah, Nilpa, et al., "Computerized Repeating and Averaging Improve the Test-Retest Variability of ETDRS Visual Acuity Measurements: Implications for Sensitivity and Specificity", Investigative Ophthalmology & Visual Science (IOVS), Dec. 2011, vol. 52, No. 13, pp. 9397-9402.

Manny, Ruth, et al., "Repeatability of ETDRS Visual Acuity in Children", Investigative Ophthalmology & Visual Science (IOVS), Aug. 2003, vol. 44, No. 8, pp. 3294-3300.

Stuart, Annie, "Facing the Myopia Epidemic", Eyenet Magazine, American Academy of Ophthalmology, Jan. 2020, vol. 44, No. 8, pp. 40-46.

* cited by examiner

FIG. 1

Evaluative Data on Myopia test patient adjusted for Emmetropia

| Date | Adjustment (diopters) | Solo Color Tests | | | 3 Color Test Scoring @ -0.1 logMar | | |
|---|---|---|---|---|---|---|---|
| | | RED | WHITE | GREEN | RED | WHITE | GREEN |
| 6-Aug | -1.00 | 20/20 | 20/16 -1 | 20/16 -2 | 40% | 70% | 90% |
| 10-Aug | -0.75 | 20/16 | 20/16 -1 | 20/16 | 80% | 90% | 90% |
| 10-Aug | PLANO | 20/16 | 20/16 -1 | 20/16 | 100% | 90% | 80% |
| 6-Aug | +0.25 | 20/16 | 20/16 | 20/16 -1 | 100% | 80% | 70% |
| 10-Aug | +0.50 | 20/16 -1 | 20/16 -1 | 20/16 -1 | 90% | 90% | 70% |
| 6-Aug | +0.75 | 20/16 -2 * | 20/16 -2 * | 20/16 -2 * | 90% | 80% | 40% |
| 6-Aug | +1.00 | 20/20 +1 | 20/16 -2 | 20/16 -2 | 60% | 60% | 50% |

\* - NOT Solo VA but rather via "Test 2" which accesses VA for each color, simultaneously

OCULAR FOCUS ASSESSMENT AND MONITORING FOR MYOPIA AND OTHER VISION DISORDERS

CLAIM OF PRIORITY

The present application includes subject matter disclosed in and claims priority to a provisional application entitled "Myopia Monitoring on a Smartphone, Tablet or other Mobile Display Platform" filed Mar. 13, 2021 and assigned Ser. No. 63/160,804, and includes subject matter disclosed in provisional application entitled "Control and Feedback of Electronic Device Reading Distance for Myopia Prevention" titled Mar. 22, 2021 and assigned Ser. No. 63/164,413, describing inventions made by the present inventors, both herein incorporated by reference.

BACKGROUND OF THE INVENTION

1. Field of the Invention

The present invention relates to optometry, and more particularly relates to the study of ocular focus issues, such as the disorder of myopia.

2. Description of Related Prior Art

Myopia (nearsightedness) has become endemic over the last decades. Severe (degenerative) myopia is a blinding condition worldwide, which can lead to retinal detachments, macular degeneration, glaucoma, and cataracts. Degenerative myopia is recognized by The National Eye Institute (NEI) and world health organizations as a key area of research for disease prevention and treatment.

Myopia typically develops during childhood. Myopia occurs due to a refractive error of the eye causes the focal point of the light to occur anterior of the retina, resulting in unfocused light being displayed onto the retina, thus leading to blurred vision. As the patient grows, the eyeball elongates along the anterior-posterior (axial direction). When this growth is unchecked, the axial length of myopic eyes becomes "too long." Once myopia develops, it tends to worsen with continued growth of the eye during the childhood years until the eye achieves its final adult dimensions. Severe myopia can result in permanent vision complications including blindness.

Public awareness of myopia complications and the potential for childhood treatment prevention is rapidly increasing. Families are requesting guidance and treatment assistance to identify and prevent the development of severe myopia in the years to come. Home monitoring of myopia progression by assessing for changes in visual acuity over time could be performed through the use of innovative mobile device software as an early indicator that myopia is worsening. This would facilitate timely referral to an eye care specialist for prevention, treatment or to modify treatment.

Most eye charts (even those on electronic devices such as computers, tablets, and smartphones) do not employ protocols or algorithms. Examiners vary in their testing procedures. Without validated testing protocols, visual acuity results vary based on the skill and experience of the proctor conducting the test. Results from eye charts without standardized testing protocols are suspect when conducted by anyone but skilled professionals, and are prone to increased test-to-test fluctuation. Increased test-to-test fluctuation without an actual true change in visual acuity reduces test sensitivity, and makes small but clinically important real changes in visual acuity resulting from myopia or other vision disorders difficult to detect.

Adaptive testing procedures manipulate testing based on previous answers, and concentrate testing close to the estimated threshold to determine an accurate and reliable end point measurement of threshold. The Early Treatment Diabetic Retinopathy Study (ETDRS) adaptive protocol is the "gold standard" for testing visual acuity. However, this is a complex and time-consuming test which requires formalized and extensive training to administer. An electronic version of the ETDRS adaptive algorithm exists for computers, but to our knowledge is not available on smartphones or mobile devices for use at home.

A standardized and automated adaptive algorithm (EYE-SPY 20/20) specifically designed to standardize visual acuity testing on smartphones has been described in a U.S. Provisional Patent Application entitled "AUTOMATED ADAPTIVE ALGORITHM METHOD TO STANDARDIZE VISUAL ACUITY TESTING AND REPORTING" filed May 5, 2020, and assigned Ser. No. 63/020,013, and the related disclosure attached, herein incorporated by reference. This algorithm employs a LogMar design and testing strategy to allow intercalation of visual acuity levels "in between" traditionally reported visual acuity lines. Since traditional visual acuity lines are typically separated by a 25% difference in size, reporting vision and monitoring for changes "in between" vision lines have the potential to add better sensitivity to detect small changes in visual acuity resulting from worsening myopia. With such specificity, the difference in focus of individual wavelengths of light becomes relevant.

White light is comprised of a multitude of light waves of varied wavelengths, experienced by humans as colors. The human eye acts as a lens in that it refracts (bends) different colors to a greater or lesser degree. Shorter wavelengths (e.g., blue or green) are refracted to a greater degree than longer wavelengths (e.g., red). White light (which includes the full visible light spectrum) would represent the overall average of light, and thus average the refractive power of the human eye as a lens system. When wearing corrective glasses to maximally focus white light on the human retina, these optical characteristics result in the focal point for green light falling slightly in front of the retina and the focal point for red light falling slightly behind the retina. If corrective lenses (glasses or contacts) are prescribed to optimally focus white light, both red and green wavelengths are each slightly blurred as they have focal points either slightly behind or slightly in front of the retina, respectively. Eyeglasses and contact lenses are typically prescribed in 0.25 diopter (dpt) increments. Worsening of myopia by 0.50 to 0.75 dpt become clinically significant enough to change eyeglasses prescriptions. The differing refractive properties of red vs. green wavelengths represent a clinically significant 0.50 to 1.00 diopters! This means if glasses are perfectly prescribed for white letters, green and red letters will both be in about equally good focus. However, as myopia worsens over time, green letter will experience defocus blurring slightly before white (and finally) red letters become blurred from defocus. When monitoring for changes in visual acuity at distance, preferential blurring of green letters (with less blurring of white or red letters) is associated with worsening myopia and increases sensitivity to detect myopia changes versus evaluating only white letters alone.

It is common practice in children and young adults to prescribe corrective lenses for myopia slightly stronger than what actually required to achieve 20/20 vision at distance (overminused). Until middle age, patients can accommodate or focus through the stronger lenses and achieve clear vision effortlessly. Prescribing slightly stronger nearsighted glasses (0.50 to 1.00 dpt) than absolutely necessary in children allows for future growth of the eye to occur without complaints of blurred vision from worsening myopia, and also helps provide better vision at night (night myopia phenomenon). However, by "over-prescribing" the amount of nearsightedness correction needed for clear vision, significantly greater worsening of the nearsightedness will need to occur before the worsening myopia is reflected as an actual change in visual acuity if only white letters are evaluated.

If nearsighted glasses are initially prescribed "too strong" "or "overminused" (whether intentionally or inadvertently), the red wavelength should appear slightly blurred as compared to the white or green wavelengths on initial baseline testing. As myopia worsens over time, the red letters would initially improve in focus (clarity) before a worsening in white letter/green letter testing becomes noticeable. Eventually, as myopia progresses far enough, the red letters will experience blurring along with the other wavelength colors. In the setting of overminused glasses, the inclusion of red letters alongside white and green letters potentially allows for an earlier detection of worsening myopia when monitoring for changes in visual acuity at home as an indicator of myopia progression.

In the eye professional's office, the main tool used to track myopia is axial length (the anterior posterior length of the eye) using a sophisticated machine. Axial length measurements are not available in the home setting. Visual acuity is one possible way to monitor for changes in nearsightedness at home. A home monitoring tool may allow evaluation for changes "in between" professional eye examinations. A HIPAA compliant communication platform between doctor and patient can help the doctor evaluate these changes and facilitate the doctor to prescribe recommended treatment alterations or schedule an office examination sooner.

However, available home visual acuity tests have various limitations which make them poorly sensitive for reliably measuring the small changes in myopia (0.50 to 1.00 diopters) which would be clinically desirable.

It is therefore a primary object of the present invention to prepare a system and method for self-guided or at-home visual acuity testing.

It is another object of the present invention to provide a method for regular testing of visual acuity and focal length.

It is yet another object of the present invention to provide an adaptive testing system utilizing various color wavelengths.

It is a further object of the present invention to provide a test to allow for visual acuity and/or focal length testing in multiple colors.

It is also an object of the present invention to monitor visual acuity and/or focal length changes.

It is also a further object of the present invention to provide an eye exam that is useful, easy to use, and allows for monitoring of clinically significant changes in focal length.

These and other objects of the present invention will become apparent to those skilled in the art as the description thereof proceeds.

SUMMARY OF THE INVENTION

As system and method for detection of myopia changes at home, or preferred location, via measuring and monitoring visual acuity changes over time employing an adaptive algorithm. The adaptive algorithm may include simultaneous display of optotypes (as generally described below) of various color(s) to determine differences in focal length for each. The algorithm may also adapt to differences in ambient conditions and testing distance. The test may include gamification to enhance user experience.

An automated adaptive algorithm method to monitor for myopia progression on an electronic platform (computer, tablet, smartphone). Baseline visual acuity (VA) and/or baseline focal lengths may be documented using a method that is independent of examiner's prior experience, expertise, or background by capitalizing on the different refractive properties of different wavelengths (e.g., blue, green, white, and/or red, etc.) of light in the visible spectrum. The method may be employed over time, wherein results may be stored on an electronic platform (computer, tablet, smartphone) or device in telecommunication with a recording apparatus, and reported. Letters or images may be simultaneously displayed consisting of different wavelengths (e.g., green, white, red, etc.) of light in the visible spectrum to capitalize on the differing refractive properties of these wavelengths. Preferably, there is a black, high-contrast, or low-contrast background. System may use longitudinal analysis of data points over time to identify a clinically significant eye sight change(s) (as opposed to test-to-test fluctuation) with creation of focal point and visual acuity graphs. Results may be communicated to a profession or predetermined threshold(s) and next step recommendations may be provided based on expert advice or preprogrammed thresholds. Testing glasses or virtual reality goggles may be used to adapt the system to shorter distances used (e.g., at home) to bring the focal point up close to allow self-administration of testing, and/or the software may adapt the size and display of optotypes based on distance and other ambient factors. When using the smartphone platform, intrinsic capabilities may be used to ensure maintenance of the desired test distance during testing. Preferably, the method is gamified (e.g., made into an interactive game) to maintain the subject's focus and attention.

First, initial visual acuity is assessed at a known distance while using white letters at known sizing. The image is then adjusted to represent the exact baseline visual acuity for white letters. Next, vision is monitored for vision changes over time. During monitoring, an illuminated screen displays at least two, or preferably three different color letters representing different visible light spectrums. Preferably three colors of optotypes (red, green and white light), are presented simultaneously, and adjacent or flanking one another, during the monitoring phases to evaluate for selective changes in visual acuity performance for each color spectrum over time suggestive of refractive focus changes consistent with myopia.

A method for myopia monitoring using different color spectra by selectively comparing responses to red letters, green letters, and white letters, preferably in a low contrast situation, to create a more sensitive tool for monitoring changes in myopia. An algorithm may first obtain a baseline visual acuity threshold level with each of the optotype colors, including white letters, and spectral color optotypes, such as red letters, and green letters. Testing continues with monitoring for changes over time while testing all three colors simultaneously (each presentation consists of three letters, one of each color). The method may include evaluating for changes in focusing of the eye over time by evaluating Visual Acuity (VA) or perceived clarity of image while evaluating two or more different color letters or images (e.g., optotypes, or other images that may serve as optotypes, such as those described herein) simultaneously (taking advantage of different refractive properties of various wavelengths).

A system for testing focal length of a patient's eye(s) via systematic testing of visual acuity or focal point via a testing screen displaying one or more optotypes. A screen may display a test of one or more optotypes. The screen may be set at a known or monitored distance from a patient, such as from the screen lens to the eye of the patient. The screen preferably displays a first optotype in color white, and at least a second optotype of a first spectral color (such as red, green, blue, etc.) flanking the first optotype. A recording device is adapted to receive patient input regarding distance between the subject and the device and/or the identification of the first and at least second optotype, such as the display device, or another device. The device should allow storage of recordings, or communication to a device that has a memory. The first spectral color is preferably red, green, or blue. Preferably at least a third optotype is concurrently displayed on the screen with the first and second optotype, the third optotype is preferably of a second spectral color. Preferably, the spectral colors of the second and third optotypes have wavelengths offset by at least twenty nanometers. Preferably, the first optotype is displayed in the center or between the second and third optotypes. Preferably the optotypes are illuminated on the screen. The second (and third) optotype(s) may be positioned lateral, or vertically from the first optotype, or otherwise flanking. A recording mechanism may be used to store patient results of identification and/or distance at subjective (e.g., best focus) clarity. A communication preferably used to transmit patient results. The recording device and communication device may all be the same as the device containing the screen. The screen may also or otherwise be incorporated into a set of virtual reality goggles.

A method for monitoring the focal length of a patient's eye, said method comprising the steps of setting a screen at a known or monitored distance from a patient, and simultaneously displaying at least two optotypes on the screen. The first optotype is preferably of a known refractive property, either generally white or a spectral color. The second optotype is preferably displayed in a specific spectral color. Preferably, a third optotype of an alternative spectral color is also used. For instance, the specific spectral color may be red, while the alternative spectral color of the third optotype is green. The patient identification/selection or distance may be recorded. We may determine a known visual acuity or focal point, or known focal points for various wavelengths of light, prior to beginning and use this information to determine the size of optotypes displayed. We may monitor the distance between the patient (eye) and the screen before setting up or during the display or recording. We may test each color individually (e.g., one at a time) or in combination with other colors in simultaneous display. Preferably, low contrast display may be employed for one or more of the optotypes. We may conduct baseline testing under set ambient conditions, after/before setting the test up. We preferably conducted the test at least twice, and record the results of patient identification. Baseline is preferably conducted at the same location or conditions of the follow-on testing (e.g., if at home, baseline also at home). Testing is preferably conducted again and again at a recommended interval of time (daily, weekly, monthly, etc.). Results are preferably communicated to a supervisor. Results may be compared over time.

A method for monitoring the focal length of a patient's eye, said method comprising the steps of establishing an initial visual acuity, focal point, or perceived clarity via display of a screen at a set distance or monitored distance from a user by simultaneously displaying two or more color optotypes, and recording an initial visual acuity, focal point, or perceived clarity for each of the at least two colors presented. This may be conducted one color at a time, or with multiple colors simultaneously displayed. The patient may be retested by simultaneously displaying two or more color optotypes, and recording a later visual acuity, focal point, or perceived clarity for each of the at least two colors presented. We may then evaluate for changes in focusing of the eye over time by comparing visual acuity, focal point, or perceived clarity of two or more different color optotypes simultaneously displayed when retesting. Further retesting may include modifying one or more characteristics of the optotype(s) (size, color, contrast, etc.) based on results from the testing or retesting. We may measure the distance of the device to the patient at patient's reported visual acuity identification or subjective best focus.

BRIEF DESCRIPTION OF THE DRAWINGS

The present invention will be described with greater specificity and clarity with reference to the following drawings, in which.

DETAILED DESCRIPTION OF THE PREFERRED EMBODIMENTS

One may utilize the known and varied refractive properties of varied color wavelengths of incoming light to detect changes in focus and thereby detect myopia or monitor the progression thereof with more specificity. Visual acuity is universally used as a measurement to determine quality of vision. Visual acuity will worsen at remote testing distances as myopia develops or increases over time, unless compensatory changes in corrective lenses, such as eyeglasses, contact lenses or other forms of optical correction are made. Visual acuity measurement is a useful tool to assess for large changes in myopia, but the inherent sensitivity of visual acuity to assess clinically meaningful changes of 0.50 to 1.00 diopters in focusing changes is not adequate when assessed in traditional ways. Even the best eye chart designs (e.g., Early Treatment Diabetic Retinopathy Study, or ETDRS) when administered by professionals have been repeatedly shown to fluctuate by three to eight letters (15%-40%) without a true change in visual acuity. Monitoring for visual acuity changes at home by non-professionals would be expected to be even less sensitive to true vision changes. Visual acuity results can fluctuate test-to-test without a true change in vision. This inherent visual acuity testing fluctuation can make small true changes in vision difficult to discern. When all three colors are tested simultaneously (one red letter, one white letter, and one green letter), we would expect spontaneous fluctuations in vision to impact all three colors in a similar random way. However true changes in nearsightedness would affect one color more than the others (typically green) with this pattern of change helping us discriminate true worsening of myopia form background test fluctuation.

The "gold standard" ETDRS chart contains five letters per line. We concentrate serial testing at the previously established visual acuity threshold and compare ten red letters, ten white letters, and ten green letters at the established threshold vision line. Tripling the standard number of tested data points at the threshold line increases sensitivity.

We also start serial testing at an "exact" LogMar value even if the value falls between standard LogMar lines. Although testing is generally separated in time, which reduces the possibility of memorization, to further guard against memorization we may randomize the order of presentation of the ten threshold letters for each color each time they are presented. In addition, although the same ten letters may be used for each particular color for consistency on repeated testing, we may pull letters from different versions of the "gold standard" ETDRS chart for each different color. Since each of the three colors are presented simultaneously, randomizing letters from different versions of the ETDRS eye charts for each color increases exponentially the total number of variations of possible letters presented simultaneously as opposed to using the same five letters for each color line. This further lessens the risk of memorization.

In the circumstances of a patient's documented color vision deficiency, the deficient color is ignored in the monitoring tool and we look at only assess the wave length spectra that are not colored deficient. White color, as a combination of many spectral colors, is still often useful in such instances, along with one or more additional spectral colors visible by the unique patient.

To improve the lack of sensitivity for traditional visual acuity testing to measure small changes in myopia, several factors can be optimized for monitoring visual acuity with an illuminated device, such as smartphones/tablets as a myopia monitoring tool:

1. Use of standardized, validated, and precise visual acuity algorithms;
2. Evaluation of different color spectrums;
3. Concentrating visual acuity testing close to physiologic threshold resolution;
4. Monitoring to control for intrinsic test fluctuation via multiple measurements;
5. Testing at remote focal lengths or artificially setting the focal point at closer distances through the use of lenses;
6. Use of lower contrast vision charts; and
7. Testing in low ambient lighting conditions.

Monitoring repeated visual acuity measurements over time with different colors should demonstrate a relative shift in performance from baseline selectively in one spectrum or as the patient's refraction (focus) changes. However, the difference in visual acuity performance with different color spectrum can be easily overcome by two factors: Accommodation and Squinting.

When red letters are presented by themselves, a young subject in best focus at a remote distance for white letters can easily accommodate to bring the red letters into perfect focus. When green letters are presented by themselves, a young subject in best focus at a remote distance for white letters may compensate by squinting to create a pinhole effect which deepens the field of focus and allow the green letters to still be identified.

To take advantage of the different refractive properties of green vs. red light in the human eye, with regards to measuring how focusing changes affect visual acuity, is best achieved by presenting different color letters simultaneously so that all different color spectrum cannot be optimally in focus at the same time via natural compensations such as squinting or accommodating.

In theory, by establishing the optimal threshold visual acuity for white letters by themselves at a fixed distance, then displaying three different color letters simultaneously at the established threshold and known distance (for example, red, white, and green optotypes), all three letters cannot be simultaneously be in perfect focus. With the white letter presented in the middle, the test subject will find best focus by accommodating to the average midpoint (which approximately represents the white letter's best refraction point as it incorporates all visible wavelengths and its average lies in between the more extreme longer or shorter wavelength spectrums of red and green). By maintaining accommodation and focus on the central white letter, compensation with squinting or additional accommodation will be discouraged as it will not improve the white letter's clarity and the slightly differing red and green letter focal points will result in slight but noticeable defocus for these colors on either side of white.

Monitoring for visual acuity changes with different color spectra simultaneously has an additional benefit to help separate intrinsic test-to-test fluctuation (noise) from true vision changes. Since all three different colors are presented on the screen (e.g., smartphone) simultaneously, changes specific to one color spectrum but not affecting the other two spectrum are likely to be real. Random fluctuation which should affect all colors equally since they are being tested simultaneously. These differences are especially important if confirmed on repeat testing (baseline and weekly or bi-weekly monitoring visual acuity assessments, for example, are always repeated for each session). Once refractive error changes become large enough, all colors are impacted.

A preferred process for monitoring focal length and myopic conditions, may include a step-by-step procedure with many tests that may be optionally used or reused. Preferably, the baseline visual acuity (VA) is initially determined by a professional eye examination/eyeglasses prescription. This VA can be input as a prescription or introduction to a software application. The software determines the appropriately sized letters/optotypes to be presented to the patient based on the distance from the device screen. To calibrate the size of the letter, a standard 20/20 8.87 mm letter is used at twenty feet. Direct proportions can be used to calculate the letter size to represent the 20/20 at other distances to reach the same arc experienced by the patient. For instance, at thirteen feet, a 20/20 letter may be projected at a size of 8.87 multiplied by the ratio of 13/20, or 5.7655 mm.

If necessary, a patient may obtain updated eyeglasses (or corrective lenses) if indicated. The app may then be registered and calibrated based on the known corrected-VA. A threshold visual acuity may be determination for each of the three colors, white (general as a combination of multiple ranging light wavelengths), and spectral colors of one or a mix or related wavelengths as can be produced by the device, that are perceived as red (specific, roughly 560-625 nm+, more preferably 590-750 nm, and most preferably 620-750 nm), green (specific, roughly 450-590 nm, preferably 490-570 nm, and most preferably 500-535 nm), and/or blue (preferably 380-500 nm, more preferably 450-495 nm), etc. letters at known distance. While statistically, twenty-foot distance simulates emmetropia, the preferred distance for indoor at home testing is approximately four meters or thirteen feet. Often thirteen feet induces an approximate 0.25 diopter change, it is important to shorten the distance due to LogMar current size limitations in commonly available smartphone screens wherein a 20/60 sized letter is the maximum that can fit on a given screen at thirteen feet due to real world constraints such as typical room size and the ability from the proctor to communicate with the test subject. If necessary, fogging goggles or virtual reality goggles may be used to fix focal points at a preset or known distance and allow for shorten testing distances. Either at the clinic or home, a color vision testing may be performed to ensure all visible color spectra used are detected by the patient.

Home testing may begin with baseline testing at the known letter height with simultaneous display of white, red, and green letters on the screen at exact white LogMar threshold (size of optotype thereby determined). Repeated later testing (e.g., weekly) may be conducted with simultaneous display of white, red, and green letters at the initial white LogMar threshold. The software may then use automated or manual data analysis and report (automated or manual) to prescribing eye professional/physician.

Numerous and repeated testing sessions over multiple days (or spanning weeks, months or years) allows for a more accurate measure of true changes in the eye's focus versus random fluctuation, as visual acuity can fluctuate from time to time based on circumstances, physical condition, etc. without an actual true change in vision. Using the system, eye testing can be repeated, or continued, at letter sizes appropriately matched to the predetermined visual acuity levels as stored in the device's memory or otherwise recorded and/or stored locally or remotely in communication with the device.

Concentrating testing of multiple data points at a previously established threshold visual acuity line (e.g., ten data points for each of the three colors or thirty data points total) would be predicted to provide more sensitivity to small changes in vision than the typical visual acuity testing methods. Repeating testing twice on each test day can help establish intrinsic test fluctuation from longer term true changes over time by establishing an average and predictive standard deviation.

Graphically monitoring changes in visual acuity performance with regards to intrinsic test fluctuation (which would be expected to increase as visual acuity worsens over time) as well as visual acuity averages versus established baseline for each color and repeated over time allows for established trends to help differentiate between random noise vs. a directional change in visual acuity (worsening trend). The more data points obtained as a result of more frequent testing (daily vs weekly vs monthly), the easier to identify true changes which can be represented graphically to help distinguish from random variation.

One method to increase data points for enhanced sensitivity would be gamification to allow self-testing at near via fogging glasses worn over corrective contacts or glasses (e.g., +2.00 sphere=focal point of 50 cm). For example, gamification may be employed where three vertically aligned basketball hoops each containing a different letter of different color. Keyboard of possible letter selections at bottom of phone display changes from red, white, or green letters to so that letter selected is assigned to the corresponding color hoop. A similar test could be customized by removing any corrective lenses for those subjects already nearsighted enough that their focal point is within arm's reach. Alternatively, virtual reality glasses could be used to induce the desired baseline focal point. Grated pictographs, such as those known in the art for grating acuity tests, may also be used without letters (the grates acting as optotypes). The size, number, contrast, and thickness (or other variables known in the art) may be modified to determine if the user can perceive the direction of the lines/grates. Points can be scored based on correct/incorrect answers, and a target/shooting game can be used to make it more fun/compelling.

Conventional eye charts are high contrast letters such as black on white. When a consistent amount of optical defocus is present, the target letter becomes harder to identify as the contrast between the target letter and the background is lessened. Children and young myopes generally have excellent contrast sensitivity. By lowering the contrast of the target letters presented, the myope with proper optical correction can still identify letters correctly, but the testing becomes more sensitive to small detecting small amounts of optical defocus (worsening myopia). Contrast levels should remain consistent for different color letters presented to capitalize on chromatic changes in focus. Although there is physiologic variation, contrast settings were determined and balanced for the different color optotypes presented through subjective input of several test subjects and will be refined as necessary based on ongoing research.

Method Details:
1. The app is designed for monitoring of vision changes at home, typically after following a complete eye examination by an eye professional.
2. A new patient is identified when newly diagnosed with myopia, identified as "at risk" for myopia, or being followed by their eye professional for myopia.
3. In most cases eyeglasses (or contacts) will be prescribed or updated by the eye professional prior to initiating home monitoring with the app. In some cases, patients "at risk" for myopia (due to family history or based on eye exam results) will be monitored at home either without a professional eye examination, after a professional eye examination during which no eyeglasses were prescribed, or in other cases the current eyeglasses/contact prescription will simply be verified as correct before initiating home monitoring.
4. The app is downloaded onto a high-resolution device capable of illuminating letters, such as a smartphone or tablet to allow home use.
5. The child/patient to be monitored is registered in the app.
6. An appropriate location is identified for testing of sufficient length (10-13 ft.) for testing, preferably away from glare of windows. A light meter may be incorporated to confirm appropriate lighting conditions and consistency of lighting condition for future testing.
7. The app may measure the appropriate test distance (e.g., 13 ft.) using the intrinsic measuring capabilities of the device, as discussed in U.S. Pat. No. 10,631,723 B1 entitled Subjective Visual Assessment system and Method, by Richard S. Tirendi, et al., issued Apr. 28, 2020, herein incorporated by reference. The app may monitor and/or maintain the correct test distance by interrupting the test or alerting the user if the test distance varies beyond pre-set parameter. Alternatively, these measurements of testing distance may be recorded by the device, or performed manually or with other measuring devices.

8. Visual acuity testing proceeds in a fashion as described below using an adaptive algorithm. Testing is generally performed one eye at a time using an eye patch or other type of occluder. There may be circumstances where it is desirable for both eyes to be tested simultaneously. The first step during initial testing is to determine three different visual acuity thresholds using the adaptive algorithm previously described as follows:
   a. Low contrast visual acuity with white optotypes,
   b. Low contrast visual acuity with green optotypes
   c. Low contrast visual acuity with red optotypes.

Although some physiologic variability in color sensitivity is anticipated, these letters (white, green, red) have had luminance subjectively calibrated in test subjects to be approximately equal.

9. In the presence of color blindness red and/or green may be harder to discern which would adversely affect testing with that color(s). Color vision impairment occurs in 5-8% of males and 0.5 to 1% of females. If a subject significantly underperforms (e.g., one LogMar line) on red and/or green letter testing compared to white letters, a color test will be performed to confirm the presence of a significant color deficiency. The app may contain an initialization color test (a number of different color tests already exist as phone apps). If a color deficiency is confirmed, ongoing testing will be only with white letters or a combination of white+green or white+red letters to eliminate ongoing testing with any of the color spectra demonstrated as impaired.

10. Baseline testing is then initiated at 13 ft. (or another set or variable distance) under the same lighting and testing conditions as were used to establish the white letter threshold. Ten presentations of three letters at a time (one white, one red, and one green) are preferably displayed simultaneously at the threshold visual acuity value determined for white letters by themselves. These results are recorded, then the testing is repeated to obtain averages and testing variation with each color spectrum.

11. Repeated testing occurs at a recommended interval (e.g., weekly or bi-weekly) in the same manner.

12. Results may be evaluated manually or by an automated algorithm. Results are communicated to parents by the app at the end of each testing session and to eye professionals either through a telehealth system or at the time of the follow up professional eye examination.

Figure 1:
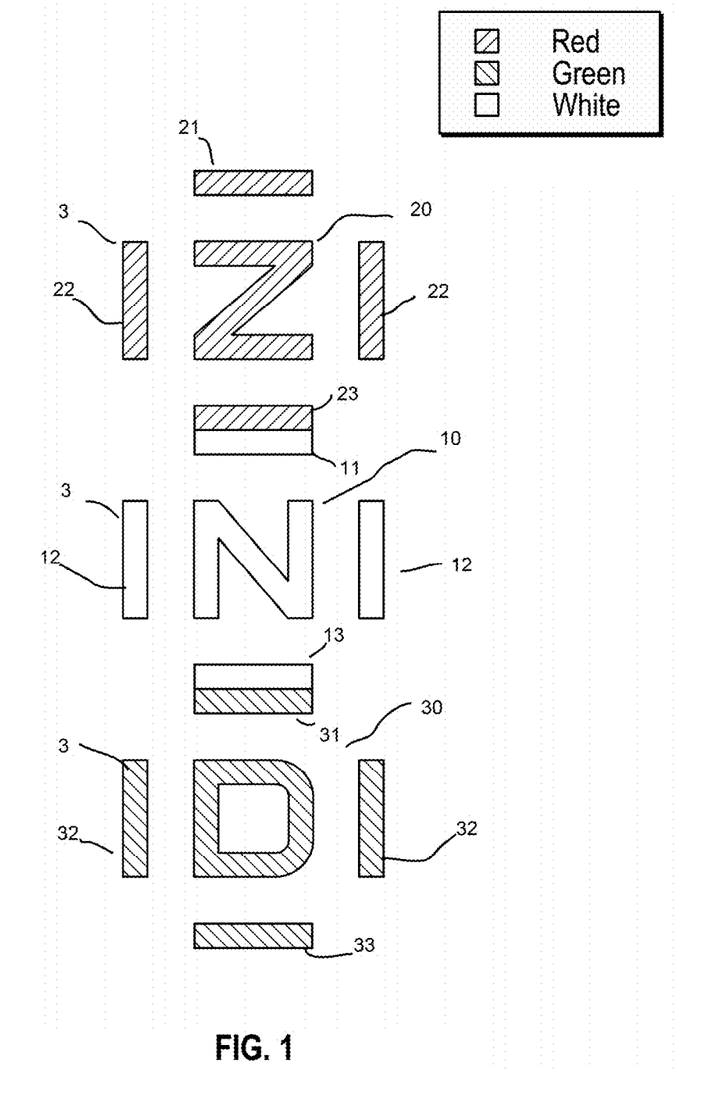
FIG. 1 illustrates a sample optotype visual display of an embodiment of the present invention.

Referring to FIG. 1, a sample test screen 1 is shown with three separate optotypes arranged vertically on a two-dimensional or curved plane. The white optotype 10 in the center (here shown as a letter "N"), and the red 20 (here shown as a letter "Z") and green 30 (here shown as a letter "D"), above and below, respectively. Crowding bars 3 are utilized between the optotypes and surrounding the optotypes. Adjacent letters when presented in horizontal rows visually interact with each other and make identifying each letter more difficult than when presented individually (crowding effect). Crowding bars similarly interact with the letters they surround to mimic the crowding effect of rows of letters when letters are presented individually. Top red 20 includes upper 21 and side crowding bars 22 in the same color red, as well as the top portion 23 of the crowding bar (red) separating the lower white letter 10. White letter 10 includes crowding bars on sides 12 as well as top portion 11 and lower portion 13 is white. Green letter 30 includes side bars 32 and lower bar 33, as well as shared portion (lower) of bar above 31 (also in green). It is preferred that the optotypes are illuminated, and the center optotype be of a common white color (incorporating all (most all) or complete perceived visible wavelengths). Background is preferably black, or low-contrast gray, or other low contrast setting/color, and darker than illuminated optotypes. The optotypes can be arranged horizontally, again with the white letter and spacer bars central and flanked by adjacent red and green on either side.

It is preferred to use at least two concurrently displayed optotypes, of differing colors. More preferably, at least three optotypes are used. A white letter is always preferred, to be complemented by one or more color letters. Red, green, and white are preferred as the red and green spectral colors are associated with cones in the retina. Blue may also be used as a spectral color, or instead of other color(s). Given that blue cones are also present in most eyes, blue color illuminated optotype may be used in substitution, or addition to the red and/or green lettering. However, it has been found clinically, due to fewer blue sensitive cones in the human eye, that red and green are the most useful to distinguish focal length in the eye, even though blue wavelengths are even shorter and thus are refracted to a greater degree.

As used herein, the term optotype or optotypes refers to images useful in the invention, as well as those known to be used in the art, and may include letters, icons, figures, artwork, picture or portion(s) thereof, logos, or images, etc., or a figure that can be projected or illuminated onto a plane or curved surface. Similarly, crowding bars may be used as are known in the art, and are preferably rectangular in shape. As in FIG. 1, crowding bars between letters may be heavier, preferably 50-100% heavier than crowding bars arranged around the optotypes, however, the crowding bars that are set between may be of similar weight as the other crowding bars. Dual color crowding bars may be used sharing the color on each side with the adjacent lettering (as shown), alternatively, a neutral color, such as white, an alternate color, or the color of the colored adjacent letter may be used for the entire crowding bar. Optotypes may be arranged vertically, as shown in FIG. 1, or horizontally, often depending on the hardware requirements (e.g., size and shape of screen. Optotypes may be arranged in any fashion useful for the test, including flanking at angles, such as when used with combined image optotypes (see, for instance FIG. 7). Optotypes are preferably illuminated to the screen. For the purposes of this disclosure, the term 'illuminated' means that the source and focus of the light carrying the optotype is at or behind the screen, primarily to distinguish reflections often used on paper poster boards known in the art of optometry. The optotypes may be backlit or edge lit, as is known in the art, and light waves emanate or reflect from behind on or the surface of the screen. The illuminated lettering/optotypes allow for computerized or digitized display that can easily be modified for test-to-test, and relate to a recording of the responses.

As used herein, it is preferred that optotypes or images or sections used for identification purposes are referred to as flanking, when the two optotypes, etc. are displayed on a screen simultaneously either adjacent, or more preferably with a portion of background or low contrast screen, and often crowding bars, outlines, or other elements, set between. As described above, optotypes may be flanking when background and crowding bars are set therebetween. Similar, as shown in FIG. 7 (described below) image sections used as optotypes may be flanking when portions of background(s) and/or other images sections and/or outlines (or even further portions of the same optotype or other optotypes with same color) are set therebetween.

The application on the local device recruits pixels in the assigned color (e.g., LED blue, red, and green on a standard tablet). Depending on desired contrast, the luminosity is adjusted by recruiting the appropriate number of pixels. For instance, half of the pixels may be recruited for a 50% luminosity, as opposed to recruiting all pixels for highest intensity. The rate of colored pixels recruited adjusts the perceived color. Low contrast, as herein used, refers to an offset in the number/portion of pixels recruited in adjacent sections or background, either more or less than the subject image/optotype. For instance, using 80%-20% pixel count in the adjacent squares will lead to a low contrast comparison. Similarly, any adjustment, down to 95%-5% change in pixel recruitment may be low contrast. Low contrast may also be achieved by modifying the wavelength of background, etc. to an alternative wavelength in adjacent images/sections by less than one to up to fifty nanometers, alone, or in combination with a change in number of pixel recruitment. In this way, a low contrast display will show the desired image adjacent or next to a background or further image with a slightly different brightness and/or color, to challenge the subject to differentiate and/or identify the image/optotype. Low contrast may also refer to the use of grating acuity for subjective best focus or objective identification, Vernier acuity, sample color blind test, etc. as is known in the art. For order of display, while red is shown on top in FIG. 1, it is preferred that consecutive displays randomize the placement/location of the red and green above/below (e.g., R-W-G, G-W-R, R-W-G, consecutively) to wash out any preferences of the patient for top-or-bottom display. Other spectral colors, e.g., blue, would similarly preferably replace one or both of the R and G.

Figure 7:
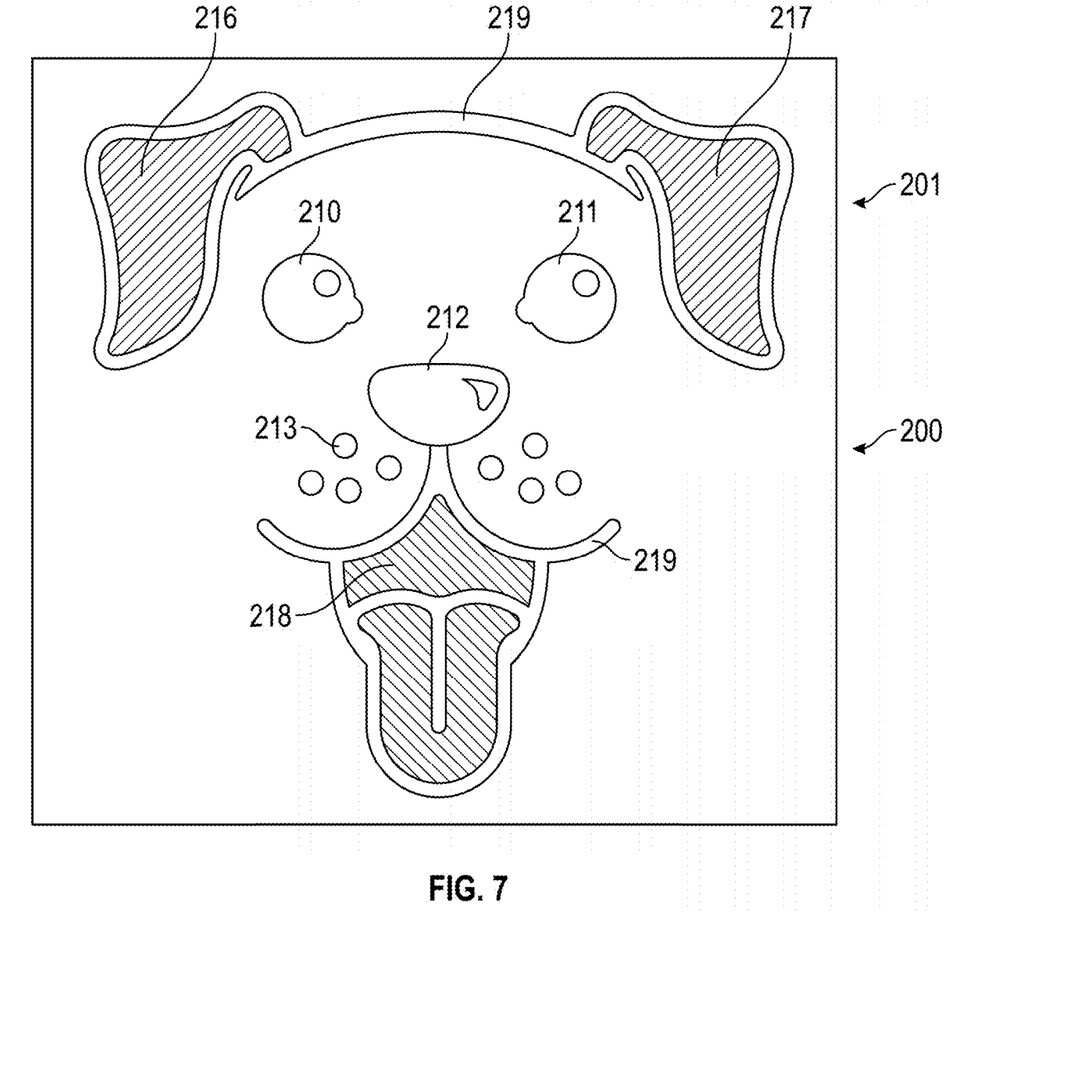
FIG. 7 illustrates an example figure image optotype useful in an embodiment of the present invention.
Figure 8A:
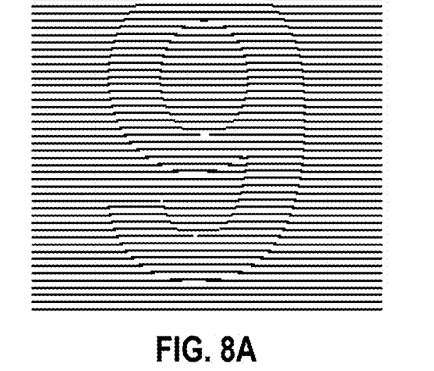
FIG. 8A illustrates an example of an embedded image useful in an optotype for the present invention.
Figure 8B:
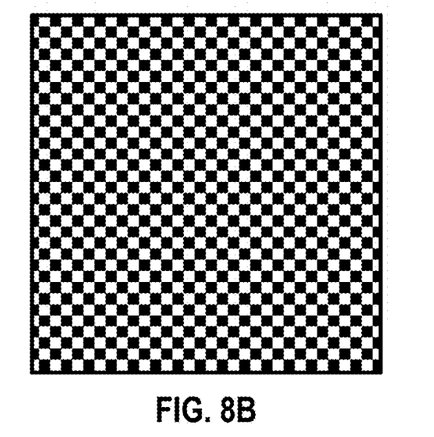
FIG. 8B illustrates another example of an embedded image useful in an optotype for the present invention.
Figure 8C:
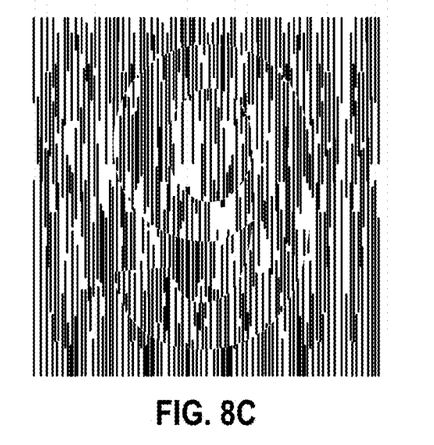
FIG. 8C illustrates another further example of an embedded image useful in an optotype for the present invention.

As shown in FIG. 7, an optotype or collection of optotypes may be incorporated in a complex image. Here, a cartoon dog face 200, is preferably set on a dark or black background 201 to provide contrast to brightened portions of the image. Image 200 may include sections of varied color, including eyes 210 and 211 set above and apart from nose 212, and whiskers 213, in white. Flanking ears 216 and 217 may be employed with a green light. A red tongue 218 illustrates a third option and color for view. Each of the optotype sections 201/211 (white), ears 216/217 (red) and tongue (218) may optionally employ an embedded or hidden message in high or low contrast, such as those shown in FIGS. 8A-8C described below. A simple letter may be written in the color, or the patient may be asked to describe the features and/or shapes of the optotypes (e.g., concave features on the upper and outer portions of the ears, a center vertical bar partially bisecting tongue, etc.). When outline gray 219 is not used, subject may identify when edges are in 'best' focus against a background, or when outlines are included, against the outline. Alternative, embedded images may be employed that are hidden in the optotypes. Solid colors, stripes (to identify the direction of the stripes or when they are in focus), a hidden image, sharp contrast edges, subjective determinations, or other designs known in the art may fill the optotypes for identification by the patient. Sharp contrast or low contrast grating or images may be employed within the optotype sections, such as those shown in FIGS. 8A, 8B, and 8C. As shown in in FIGS. 8A-8C, the number "9" is employed in sharp contrast (FIG. 8A) and in low contrast (see FIGS. 8B and 8C). As shown in FIG. 8B vernier acuity may be tested. The measured distance to allow for proper or subjectively best focus of the embedded image in each may be recorded (as in when the patient may move closer/farther to get best focus). Alternatively, at a set distance to screen, as may be set by baseline, may be used to measure patient's ability to recognize the embedded image and thus measure visual acuity in each color. Future testing may allow the patient to modify the distance to achieve proper focus, and such modification of distance will be recorded for patient to achieve subjective best focus.

It is preferred that the size of the optotypes is determined and displayed according to the registered user. The size of the optotypes will correspond to the prescriptive eyesight of the user (e.g., 20/20 vision) and the distance of the device/screen when testing is conducted. It is preferred that a single distance is used in all testing, and from time-to-time as testing recurs. The ambient conditions should also be as close as possible to the initial and consistent in other testing sessions. However, the adaptive algorithm may modify the brightness, size, and other parameters of the displayed optotypes based on sensing of ambient conditions, and distance from the patient (e.g., pupil, retina, face, etc.), angle of incidence, etc. In addition, the algorithm may adapt to changes in VA, for instance to make the letters slightly larger as myopia progresses or as determined by a supervising physician. Preferably, the patient test includes serial display of a multitude of screens. The system preferably records the perceived optotype (patient's proposed answer) with a local device, or by oral transmission to the display device, or otherwise. It is preferred that a gamification occurs with the display screen, for instance, using correct or responsive answers to progress an in-game score, or the like, as is known in the art of participatory and competitive gaming. Multiple screens are to be displayed in serial fashion to eliminate statistical anomalies and garner a more realistic and accurate assessment of the eyesight of the patient. The testing is preferably repeated with the same size optotypes, preferably on a weekly or bi-weekly basis. As time progresses over multiple tests a change in the patient's eye sight may trend.

Figure 6:
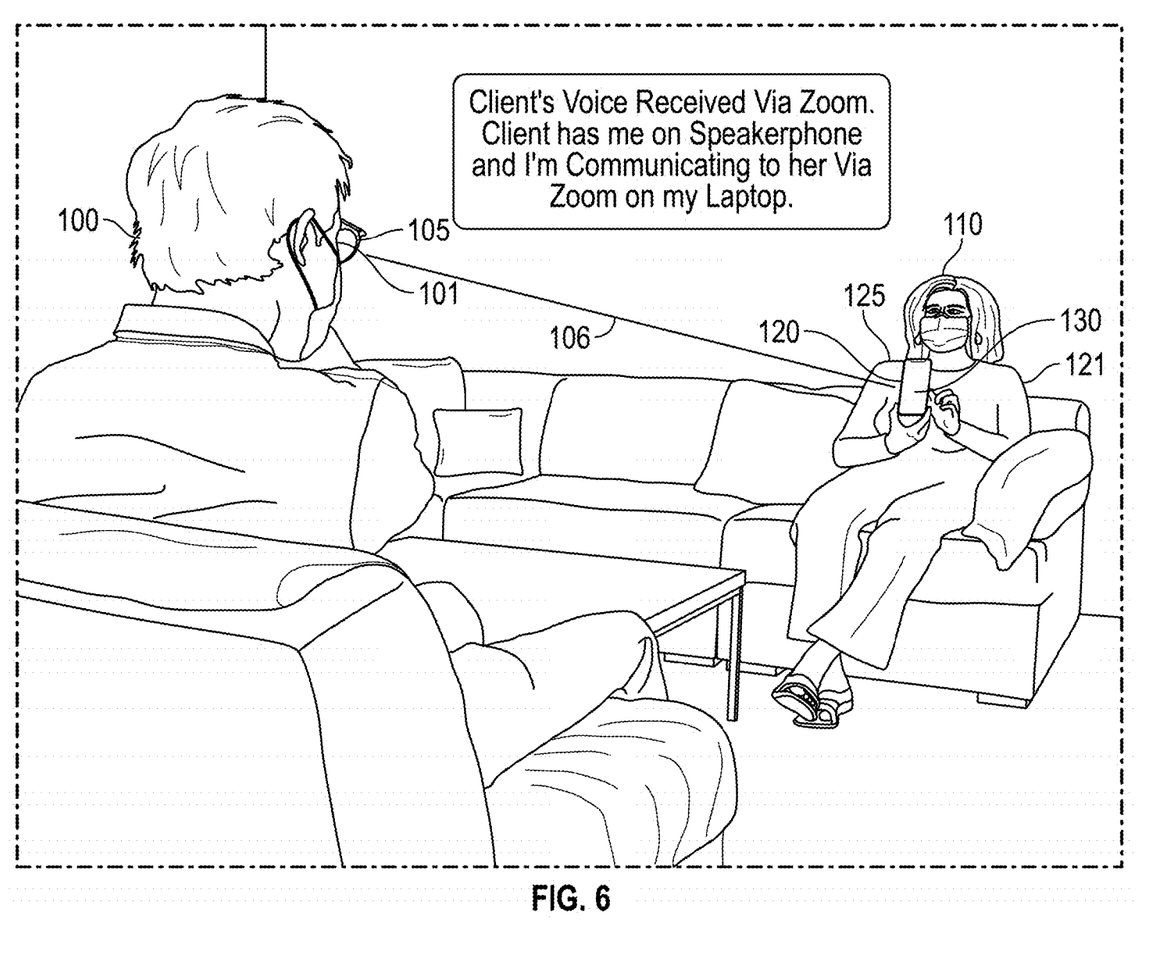
FIG. 6 demonstrates a perspective view from behind a test subject in front of a proctor at a typical clinical setting.

As shown in FIG. 6, test subject, or patient, 100 may be positioned in a set location 105, with eyes 101 in known position. The proctor 110 is an optional feature, as the screen 120 may be positioned and set on a surface, or otherwise mounted or established in place 121. The distance 106 between the eyes 101 and the screen is preferably determined (and may be recorded) by device 125 with onboard memory and computing as is known in the art, for such devices as smart tablets, smart phones, etc. It is contemplated that similar devices and methodology employed in U.S. Pat. No. 10,631,723 herein incorporated by reference, are employed. The distance may be measured, and the optotypes 130 may be size in accordance with known or measured distance 106. In some embodiments of the present method, the dynamic real time size is employed on screen for optotype size/shape, etc. Optotypes 130 are displayed on screen 120, wherein patient 100 either manually, electronically, or audibly (or by means conceived or described in U.S. Pat. No. 10,631,723) provides answers. Answer can be recorded by the device (for instance received by a microphone), outside the device, or recorded by proctor (when present). It is contemplated that the present method may be employed by the test subject alone, or with a proctor, and may employ additional assistants to monitor, measure, or record answers/identifications.

Recording may occur in one or more devices, e.g., phones, linked via wired or wireless telecommunications (e.g., Wi-Fi, Bluetooth, telephone, etc.) to record answers. For instance, patient may have a handheld device (smart or simple mechanical/electrical button to record answers which can be communicated to screen deice, or to a third device). Alternative, patient can record answers audibly or mark them down manually (e.g., pencil/paper), or other method described or referred to herein.

Patient may be outfitted with ocular devices such as a virtual reality (VR) headset as is known in the art, or augmented reality (AR) may be employed to display optotypes or otherwise portions of a game that may be played by patient as the testing commences. For instance, correct answers, or identification may be used to move real-time objects in the viewers perception through the VR or AR experience. When using VR, the screen may be employed within the headset, with a known lens used to focus, and the technology of U.S. Pat. No. 10,631,723, or other analogous methodologies known in the art, may be employed to properly size and display optotypes for view and assessment. Distance to the image is preferably used to indicate distance to image and size requirement, adapted/modified by known focal length of lens or lenses employed within the VR headset. Either in VR, AR, or with a hardware device, the distance from screen (or perceived screen) may be modified by the patient until focus is achieved (and recorded). When using VR or AR, the perceived distance may be modified by the patient, or a proctor, until patient records satisfactory distance/size of image to allow for proper focus. For instance, patient may use a selfie-stick, as is known in the art, to physically control distance and position of the device (and/or screen), particularly for games, such as AR games. The on-board software application may measure the perceived distance (or virtual distance) to the letters and thus correctly measure VA. Preferably, device can measure distance to screen in one-to-two-centimeter distances, or more preferably to the millimeter. A one-to-two-centimeter difference may be enough to distinguish the varied focal length of various colors, when device is set at preset distance. Methods described in U.S. Pat. No. 10,631,723 may be employed, LIDAR, or other means known in the art to measure distance. The white optotype may not always be positioned in the middle, particularly when using VR goggles. Simultaneous display of optotypes with different wavelengths may be shown, and the system analyze the different focus properties associated with each wavelength/color.

Figure 2:
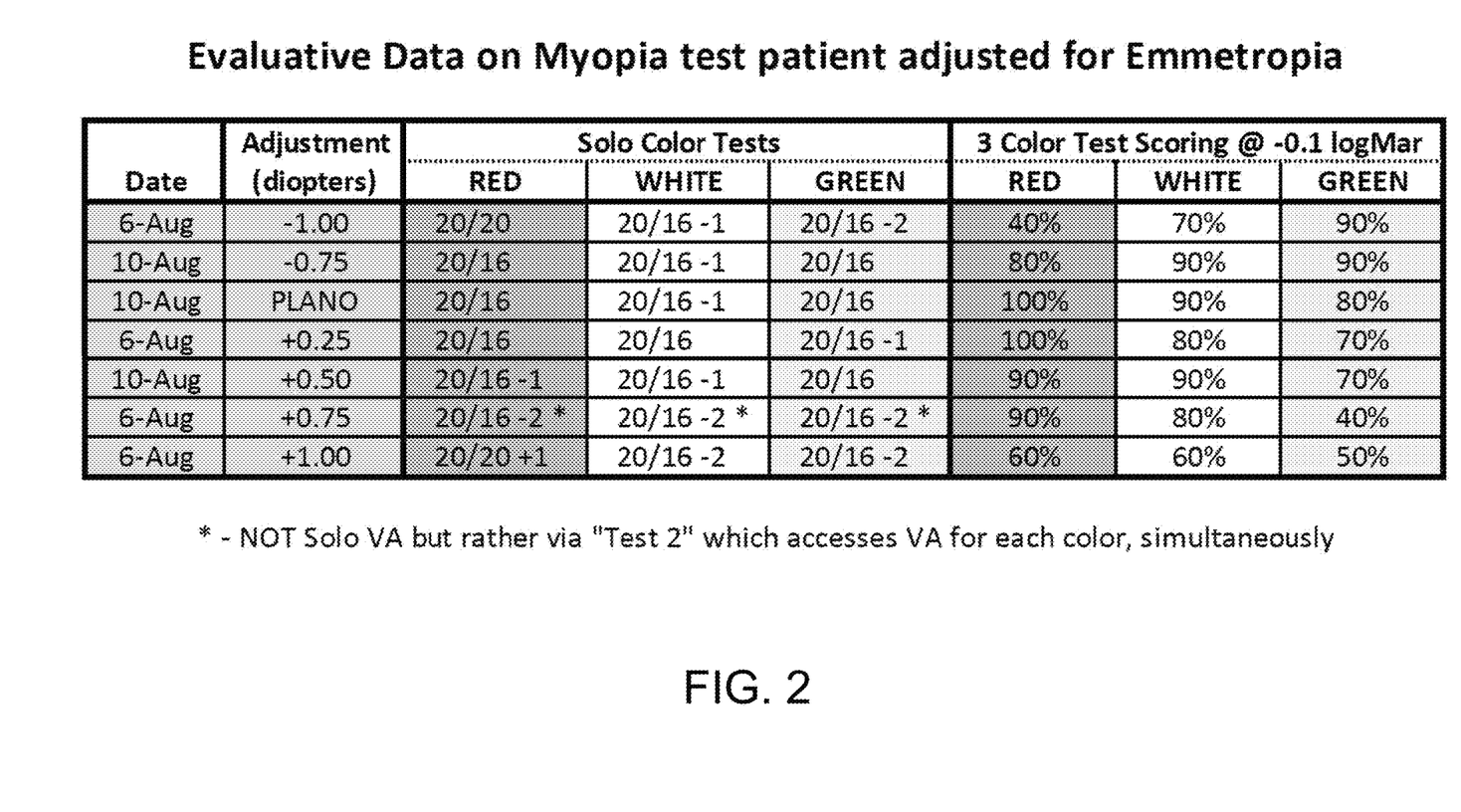
FIG. 2 is a table showing evaluative data on myopia testing.

As is shown in FIG. 2, an actual pilot patient was tested using two different methodologies with the red, white, and green optotypes used individually (one color at a time with one or more optotypes) or in combination (e.g., red/green, red/white, red/white/red, green/white, green/white/green. or red/green/white) to demonstrate the differing impact on VA by color when myopia (nearsightedness) or hyperopia (farsightedness) is artificially induced (Evaluative Data on Myopia test patient adjusted for Emmetropia). Testing was performed August 6$^{th}$ and later on Aug. 10, 2021. The patient (PLANO meaning without trial lens adjustment on August 10th) scores at about 20/16 for all three-color letters when presented as one single color at a time. Adjustments are made with trial lenses from −1.00 (artificially induced hypermetropia) to +1.00 (artificially induced myopia) to modify VA. The artificially induced VA changes were evaluated for all three colors when presented one at a time, and again when all three colors were presented simultaneously.

For example, +0.75 artificially induces a myopia that causes eyesight VA to minimally worsen to '20/16-2' for all three colors when tested one color at a time. But when the same +0.75 lens adjustment is used to assess VA with all three colors presented simultaneously, the results for spectral color green vary significantly from white and red. The myopic condition is not necessarily noted in the red and white colors (90% and 80%, meaning nine out of ten and eight out of ten scored correctly), but is selectively more noticeable in the green color underperformance (40%). This demonstrates that measuring vision simultaneously with three different colors accentuates the selective blurring effect of trial glass lenses as opposed to assessing vision with each color one at a time.

Another example in the opposite direction would be employing a −1.00 trial lens (induced hypermetropia or farsightedness). The VA performance for different colors begin to show only mild differences when tested one color at a time, but when all three-color test scoring is conducted simultaneously the changes are accentuated and the spectral red color (40%) scores much worse than white (70%) or green (90%). Finally, with great enough change all colors are sufficiently out of focus to impact VA performance on all colors, as in the +1.00 adjustment, where all colors score similarly distorted/unfocused (R/W/G at 60%/60%/50%).

Based on actual patient results, testing red, white, or green colors individually is less sensitive to the detection of optical blurring of VA from artificially induced myopia or hyperopia than when all three colors are evaluated simultaneously.

Figure 3:
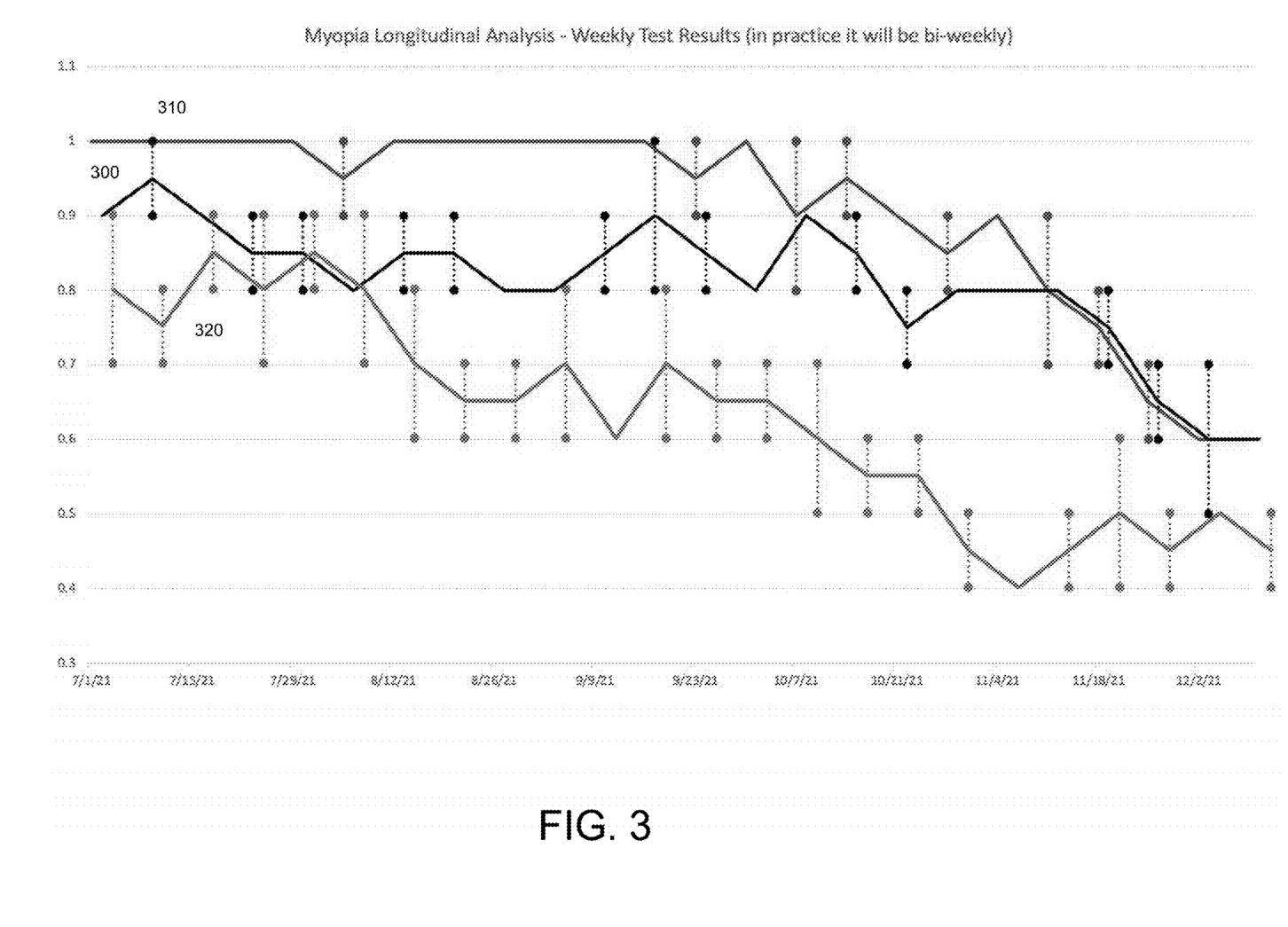
FIG. 3 graphically illustrates a first patient five-month progression of eye sight in various wavelengths of light.
Figure 4:
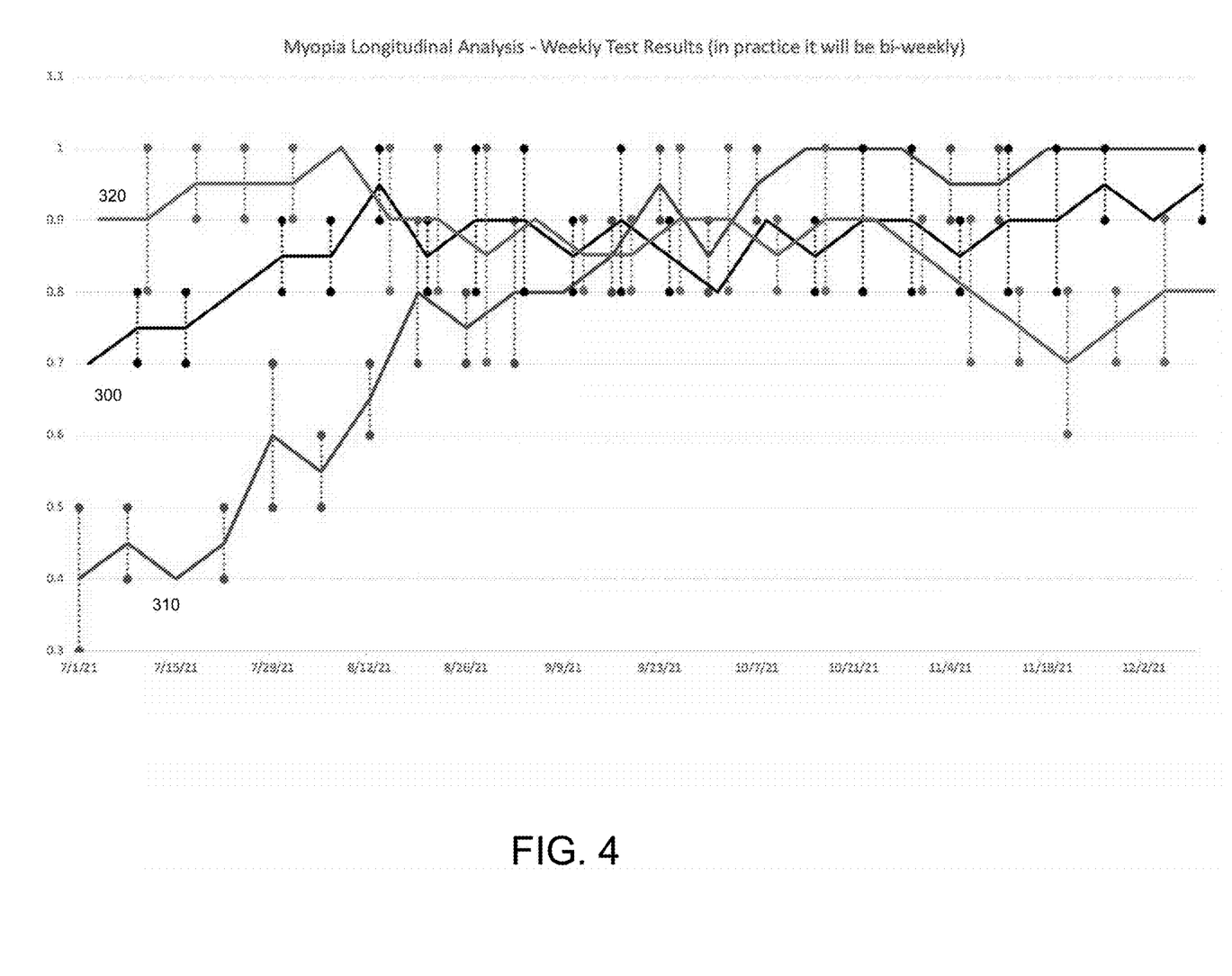
FIG. 4 graphically illustrates a second patient five-month progression of eye sight in various wavelengths of light.

As illustrative examples, FIGS. 3 and 4, Myopia Longitudinal Analysis—Weekly Test Results were shown to monitor for myopia worsening over a five-month period for each of the three colors displayed (red, green, white). Perfect score of 1 (or 100%) reflects accurate identification of all optotypes by patient in at a session. Each of the lines, red 310, green 320, and white 300 demonstrate the accuracy of the patient for that particular color optotype over a single testing session.

In FIG. 3, the value of assessing three different colors simultaneously to monitor for progression of myopia is shown for a patient with glasses prescribed close to perfect focus at the onset of testing. Scoring percentage is based on the number of correct identifications. At the outset, there was little to no error in each different color. However, monitoring visual acuity performance over time shows changes as myopia worsens, with green color selectively impeded first as green is refracted (bent) by the optics of the human eye to a greater extent than white or red colors. The initial performance changes from 100% red, 90% white, and 80% green, to about 80% red and white, and 45% green in the span of three-and-a-half months. After that, continued worsening of myopia results in degraded performance with all three colors by five months.

As shown in FIG. 4, the alternative graph shows the value of assessing for performance changes with multi-color analysis to establish a progression of myopia when glasses are initially prescribed "too strong" (which is common practice). Initially, the glasses are over compensated, such that the green letters require the least focus adjustment (accommodation) to focus them on the retina, and are most easily discernable for the patient. The red letters require additional focusing compared to white and especially green as the red wavelength is refracted (bent) less by the optics of the eye. However, as the myopia progresses over time, the longer red wavelength is gradually put into better focus on the retina. Initial underperformance of the red letters (green 90%, white 70%, and red 40%) with over-minused (too strong) nearsighted glasses improves over time (green 80%, red 100%, and white 95%). The initially over-minused patient gradually improves performance with red letters as their myopia worsens and the glasses are no longer "too strong". Note the improvement in red letter performance occurs prior to the myopia changes becoming so great as to cause a deterioration in green or white letter performance. Analyzing all three colors simultaneously allows for a more sensitive indicator of myopia worsening than could be achieved by evaluating only green or white letters in the setting of overminused (too strong) glasses, but this effect is only noted by evaluating all three colors simultaneously because if red letters were presented in isolation the patient would simply accommodate more to see them clearly.

Figure 5:
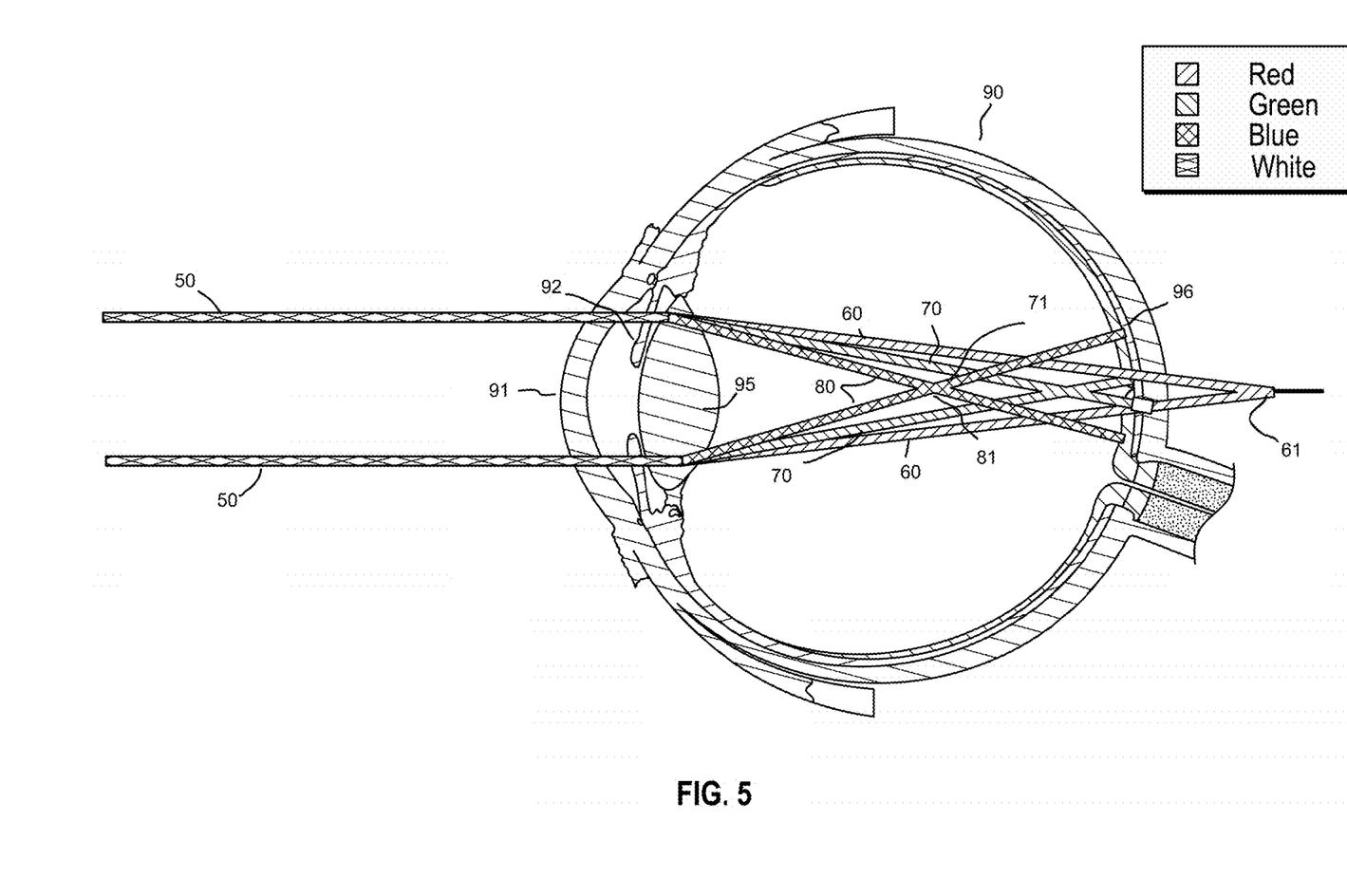
FIG. 5 illustrates a side cross-sectional view of an eyeball demonstrating the varied refractive paths of individual wavelengths of light.

The progression of myopia in the varied colors wavelengths of light is shown in FIG. 5 demonstrating the varied refractive nature of alternative color wavelengths of light entering the eyeball 90 (presumably at emmetropia). Chromatic aberration occurs with statistically equivalent parallel white light 50 (representing a combination of many spectral colors) entering in through the cornea 91 and passing through the iris 92 and focused/refracted at lens 95. Each of the light waves red 60, green 70, and blue 80, split and are refracted at lens 95 at the corresponding refractive index of corresponding to each wavelength of light. The focal point of each wavelength of light is shown where the two lines meet, such as at 61, 71, and 81. A focused visual experience occurs where the focal point corresponds with the distance from the lens 95 to retina 96, as would be shown with a focal point (lines crossing) at the retina. Blue 80, and less so green 70, light waves tend to focus anterior of the retina 96 at 71 and 81, resulting in as myopic unfocused, while red wavelengths 60, with longer wavelengths of light, tend to focus past the retina 96 at focal point 61, and display hypernietropic unfocused vision. As the eyeball 90 progresses into myopic disorder, either by changes to muscle, stiffening of lens, axial length of eye, or otherwise, what was previously hypermetropic red wavelengths tend to enter into focus as all three focal lengths are shorted (as would be shown by a leftward movement of focal points 61, 71, and 81. As myopia progresses, the blue 80 and green 70 wavelengths tend to exacerbate the shortened focal length and continue (or deteriorate) focus. Similarly, as myopia progresses, what was once hypermetropic red eyesight initially becomes more focused (until myopia progresses to the point of the red wavelengths focusing on within the eyeball short of the retina causing extreme unfocused vision). In this manner, we can see that even though a patient may be experiencing improving eyesight (in the red wavelength) this may be indicative of disorder progression (in the short term). A myopic patient thus would experience initial improvement in red, while green worsens, until all wavelengths become unfocused.

Selectively evaluating different light wavelengths (colors) to evaluate for changes in focus over time does not need to be restricted to traditional visual acuity chart assessments at a fixed distance. U.S. Pat. No. 10,631,723 (incorporated by reference) describes how subjective point of best focus can be determined by slowly moving an electronic device closer or further away from a test subject and registering the subject's response. This procedure can be expanded to include the simultaneous evaluation of different visual stimuli incorporating two or more different wavelengths (colors). For example, in addition to traditional visual acuity, vernier acuity (the ability to detect a small offset in a series of lines), grating acuity (the ability to distinguish progressively smaller spacing between parallel lines) or simply drawing or photos containing several different colors could be employed to determine both the position of best focus point for each color, and monitor for changes in the location of best focus point for each color over time. In some visual conditions such as myopia (inability to see at distance), or presbyopia (loss of ability to see at near), such testing could be performed easily at near on a mobile electronic device. In other circumstances, it might be desirable to set the focal point at a specific location (such as at near) using corrective lenses such as glasses, contacts, or incorporated into virtual reality goggles to allow for monitoring of changes in the patient's best focus point over time.

We claim:

1. A system for testing focal length of a patient's eye(s) via systematic testing of visual acuity or focal point via a testing screen displaying one or more optotypes, said system comprising:
   a. a screen displaying a test, said screen set at a known or monitored distance from a patient;
   b. a first optotype displayed on said screen, said first optotype displayed in white;
   c. at least a second optotype of a first spectral color displayed on the screen flanking the first optotype;
   d. an at least third optotype concurrently displayed on the screen with the first and at least second optotype, the at least third optotype of a second spectral color, wavelengths of said first and second spectral colors differing by at least twenty nanometers; and
   e. a recording device adapted to receive patient input regarding distance between the subject and the device and/or the identification of the first and at least second optotype.

2. The system as set forth in claim 1, wherein said first spectral color is red.

3. The system as set forth in claim 1 wherein said first optotype is displayed central to said at least second optotype and said at least third optotype.

4. The system as set forth in claim 1, wherein the first spectral color is red and the second spectral color is green.

5. The system as set forth in claim 1 wherein the first and at least second optotype are illuminated.

6. The system as set forth in claim 1 further comprising a recording mechanism to store patient results of identification and/or distance at subjective clarity.

7. The system as set forth in claim 1 wherein said screen is incorporated into a set of virtual reality goggles.

8. A method for monitoring the focal length of a patient's eye, said method comprising the steps of:
   a. setting a screen at a known or monitored distance from a patient;
   b. initially testing a white optotype and at least one specific spectral color optotype individually;
   c. after said step of initially testing simultaneously displaying at least two optotypes, including a first optotype in with light of a known refractive property, and a second optotype in a specific spectral color, on the screen;
   d. recording patient identification of at least one of the at least two optotypes or distance.

9. The method as set forth in claim 8, including the step of determining a known visual acuity or focal point, or known focal points for various wavelengths of light, prior to said step of setting, and further projecting the at least two optotypes at a size determined by said step of determining during said step of simultaneously displaying.

10. The method as set forth in claim 8 further comprising the step of monitoring the distance before said step of setting or during said step of simultaneously displaying or during said step of recording.

11. The method as set forth in claim 8, whereby said step of setting a screen employs the use of virtual reality goggles.

12. The method of claim 8 wherein said step of initially testing is conducted at low contrast.

13. The method as set forth in claim 8 further comprising the step of baseline testing under set ambient conditions, after/before said step of setting, whereby said step of simultaneously displaying is conducted at least twice, and results of patient identification are recorded.

14. The method as set forth in claim 13, further comprising the step of further testing at a recommended interval of time.

15. The method as set forth in claim 13, further comprising the step of communicating results of patient identification.

16. The method as set forth in claim 13 further comprising the step of comparing results from said step of simultaneously displaying and the second or any additional steps of simultaneously displaying.

17. The method as set forth in claim 8, whereby said step of simultaneously displaying includes displaying the first and second optotype in a flanking relationship.

18. The method as set forth in claim 8, whereby said step of simultaneously displaying further includes displaying a third optotype of an alternative spectral color, said first optotype center, with second and third optotypes flanking said first optotype.

19. The method as set forth in claim 18, whereby the specific spectral color is red, and the alternative spectral color is green.

20. A method for monitoring the focal length of a patient's eye, said method comprising the steps of:
   a. establishing an initial visual acuity, focal point, or perceived clarity of one eye of the patient via display of a screen at a known effective distance from a user at a first time, wherein said step of establishing comprises simultaneously displaying two or more color optotypes to the one eye, and recording an initial visual acuity, focal point, or perceived clarity for each of the at least two colors presented;
   b. retesting visual acuity, focal point, or perceived clarity of the one eye via display of a screen at a set distance from a user at a second time, wherein said step of retesting comprises simultaneously displaying two or more color optotypes to the one eye, and recording a later visual acuity, focal point, or perceived clarity for each of the at least two colors presented;
   c. evaluating for changes in focusing of the one eye over time by comparing visual acuity, focal point, or perceived clarity of two or more different color optotypes simultaneously displayed from said step of establishing and said step of retesting.

21. The method as set forth in claim 20, further comprising the step of further retesting by modifying one or more characteristics of the optotype(s) based on results from said step of retesting.

22. The method as set forth in claim 20, whereby said steps of establishing and retesting comprise measuring the effective distance of the device to the patient at patient's reported visual acuity identification or subjective best focus.

23. The method as set forth in claim 20 whereby said screen comprises display of via virtual reality goggles.

* * * * *